(12) United States Patent
Nelson

(10) Patent No.: US 7,589,280 B2
(45) Date of Patent: Sep. 15, 2009

(54) ELECTRICAL CONNECTOR ASSEMBLY

(75) Inventor: Charles Scott Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 11/166,296

(22) Filed: Jun. 24, 2005

(65) Prior Publication Data

US 2006/0288806 A1     Dec. 28, 2006

(51) Int. Cl.
*H02G 15/02* (2006.01)
(52) U.S. Cl. .................................. 174/84 C; 73/23.31
(58) Field of Classification Search .............. 174/84 C; 73/23.31
See application file for complete search history.

(56) References Cited

U.S. PATENT DOCUMENTS

| | | | | |
|---|---|---|---|---|
| 4,627,490 A | * | 12/1986 | Moore ........................ 166/65.1 |
| 5,817,920 A | * | 10/1998 | Kuisell et al. .............. 73/23.31 |
| 6,082,175 A | * | 7/2000 | Yoshikawa et al. ......... 73/23.31 |
| 6,322,681 B1 | * | 11/2001 | Weyl .......................... 204/424 |
| 6,453,726 B1 | * | 9/2002 | Gutierrez et al. ........... 73/31.05 |
| 6,613,208 B2 | * | 9/2003 | Vargo et al. ................. 204/428 |
| 6,672,136 B2 | * | 1/2004 | Kojima ....................... 73/31.05 |
| 6,866,517 B2 | * | 3/2005 | Kimata et al. ................. 439/33 |

* cited by examiner

*Primary Examiner*—Chau N Nguyen
(74) *Attorney, Agent, or Firm*—Paul L. Marshall

(57) ABSTRACT

A connector assembly for a planar sensing element of an exhaust gas sensor is shown, with a method for assembling. There is an opposed pair of ceramic clamshells which retain terminals, each terminal mates to corresponding contact pads of the planar sensing element. A spacer is positioned between clamshells and a seal. A retainer clip binds the ceramic clamshells. These components are contained within an upper shield, upon assembly. The spacer creates a hinge point between the clamshell devices, allowing insertion of the sensing element without abrasion or scraping of the contact pads against the terminals The retainer clip, with radially extending tabs, keeps the opposed pair of ceramic clamshells under compression upon the sensing element when assembled, due to an interference fit with the upper shield of the sensor.

14 Claims, 3 Drawing Sheets

ELECTRICAL CONNECTOR ASSEMBLY

TECHNICAL FIELD

This invention pertains generally to electrical connection systems, and more specifically to an electrical connector assembly for multiple wires in a high temperature, high vibration environment.

BACKGROUND OF THE INVENTION

Sensors used to monitor exhaust of a modern internal combustion engine are subject to stringent customer requirements and severe operating conditions which drive sensor design and material considerations. Requirements include limitations on space volume, sensor operating temperatures ranging from −40 C to greater than 1000 C, operating vibrational inputs in the range of 0 to 2000 Hz and 29 g's of force.

A typical sensor includes a planar sensing element contained in a sensor body or shell. A wiring harness is attached to the sensor, for connecting a plurality of lead wires to the sensing element. A modern sensor, e.g. a sensor capable of monitoring exhaust gas constituents including NO and $NO_2$, may require eight lead wires to the sensor element. These lead wires supply electrical energy for heating the sensor and gather signals from the sensing element, and typically interface with an electronic controller. Such signals from the sensing may include air/fuel ratio, and concentrations of various exhaust gases, including NOx.

Skilled practitioners are continually faced with the challenge of designing a connection scheme that connects the plurality of wiring harness lead wires to the sensing element, meets the stringent customer requirements for packaging size, and is robust to the severe operating conditions over the life of the engine. Another challenge in system design includes a need to prevent crossover 'talking' or interference between the various electrical signals, to ensure that signal integrity is maintained for the each of the outputs from the sensing element. There is a need to reduce errors during manufacturing and assembly of the connection scheme, and to make the various components robust to minor deviations in manufacturing tolerances.

One design constraint of importance is the diameter of the lead wires, compared to the sensing element. The sensing element size and design is driven by durability, signal integrity and response time, element warm-up characteristics, packaging constraints, and other concerns. A typical sensing element has a width of four to six millimeters, whereas typical lead wire is twenty-two (22) gage meaning a nominal diameter of 1.5 millimeters, based upon concerns for durability and strength. When twenty-two gage lead wire is used, the sum of the diameters of four wire leads (typical for a stoichiometric sensor) is six millimeters, which equals the width of the sensing element. Such density of lead wires introduces problems of mechanical and electrical interference between adjacent lead wires, and may interfere with the ability to attach wires to the sensing element. This has been addressed by placing contact pads on both sides of a planar sensing element to reduce lead wire density. However, a six millimeter wide sensing element having eight contact pads requiring attachment of eight wire leads ends up having the same problem of lead wire density.

Therefore what is needed is a scheme to connect a wiring harness to a sensing element, especially a planar sensing element with eight lead connections, for use in an engine exhaust environment that is robust to extreme temperature and vibration inputs over the life of the engine, meets stringent customer requirements, is robust to variations in the manufacturing and assembly processes, and maintains signal integrity.

SUMMARY OF THE INVENTION

In accordance with the present invention, a connector assembly for a planar sensing element of an exhaust gas sensor is shown. The connector assembly includes an opposed pair of ceramic clamshells, wherein each clamshell is operable to mechanically retain and electrically isolate a plurality of terminals and each terminal electrically conductively mate to one of a plurality of corresponding contact pads of the planar sensing element. Each of the terminals is electrically and mechanically connected to one of a plurality of electrically conductive lead wires leading to a wiring harness. There is a spacer positioned between the opposed pair of ceramic clamshells and a seal, with the electrically conductive lead wires passing through the seal and the spacer. There is a retainer clip that is operable to bind together the opposed pair of ceramic clamshells. The opposed pair of ceramic clamshells, the spacer, the seal, and the retainer clip are contained within an upper shield.

Another aspect of the invention includes the spacer operable to mechanically secure each electrically conductive lead wire and electrically isolate each electrical connection to each of the terminals.

Another aspect of the invention includes the spacer operable to substantially physically secure each of the terminals in the corresponding ceramic clamshell.

Another aspect of the invention includes the spacer able to create a hinge point between the clamshell devices prior to assembly of the connector assembly to a shell housing the planar sensing element of the exhaust gas sensor.

Another aspect of the invention includes an upper insulator operably connected to the planar sensing element able to effect a position assurance of the sensor element and opposed pair of clamshells upon assembly of the connector assembly to the planar sensing element of the exhaust gas sensor.

Another aspect of the invention includes the seal, comprising an elastomeric device with the plurality of electrically conductive wires passing therethrough and operable to substantially effectively seal the connector assembly within the upper shield.

Another aspect of the invention includes the retainer clip operable to maintain the opposed pair of ceramic clamshells under compression force when a first end of the planar sensing element is placed therebetween.

Another aspect of the invention includes an assembled sensor with an embodiment of the invention including the connector assembly and the planar sensing element, wherein the retainer clip includes a plurality of tabs extending radially from the retainer clip, and the tabs fit interferingly with an upper shield of the sensor.

Another aspect of the invention includes a method for assembling the connector assembly and planar sensing element of an exhaust gas sensor, comprising assembling the connector assembly, wherein the spacer substantially secures each of the terminals in the corresponding ceramic clamshell device, and, wherein the spacer creates a hinge point between the opposed pair of clamshell devices. The first end of the planar sensing element is inserted between the opposed pair of clamshell devices so the first end of the planar sensing element is proximally near the spacer. The opposed pair of clamshell devices are closed, causing each of the terminals in the corresponding ceramic clamshell device to mate with one of the contact pads of the planar sensing element. A distal end of each of the clamshells is substantially in physical contact with the upper insulator 7 that is physically and operably connected to the planar element 38. A compressive force is applied to the opposed pair of clamshell devices, and the compressed opposed pair of clamshell devices are secured with a retainer clip. The connector assembly assembled to the planar sensing element is inserted into an upper shield of the sensor, and the upper shield is attached to a shell housing the connector assembly assembled to the planar sensing element. The retainer clip securing the compressed opposed pair of clamshell devices has radially extending tabs that create a compressive force upon the connector assembly assembled to the planar sensing element by an interference fit when inserted into the upper shield. These and other aspects of the invention will become apparent to those skilled in the art upon reading and understanding the following detailed description of the embodiments.

BRIEF DESCRIPTION OF THE DRAWINGS

The invention may take physical form in certain parts and arrangement of parts, the preferred embodiment of which will be described in detail and illustrated in the accompanying drawings which form a part hereof, and wherein.

DETAILED DESCRIPTION OF THE EMBODIMENT

Figure 1:
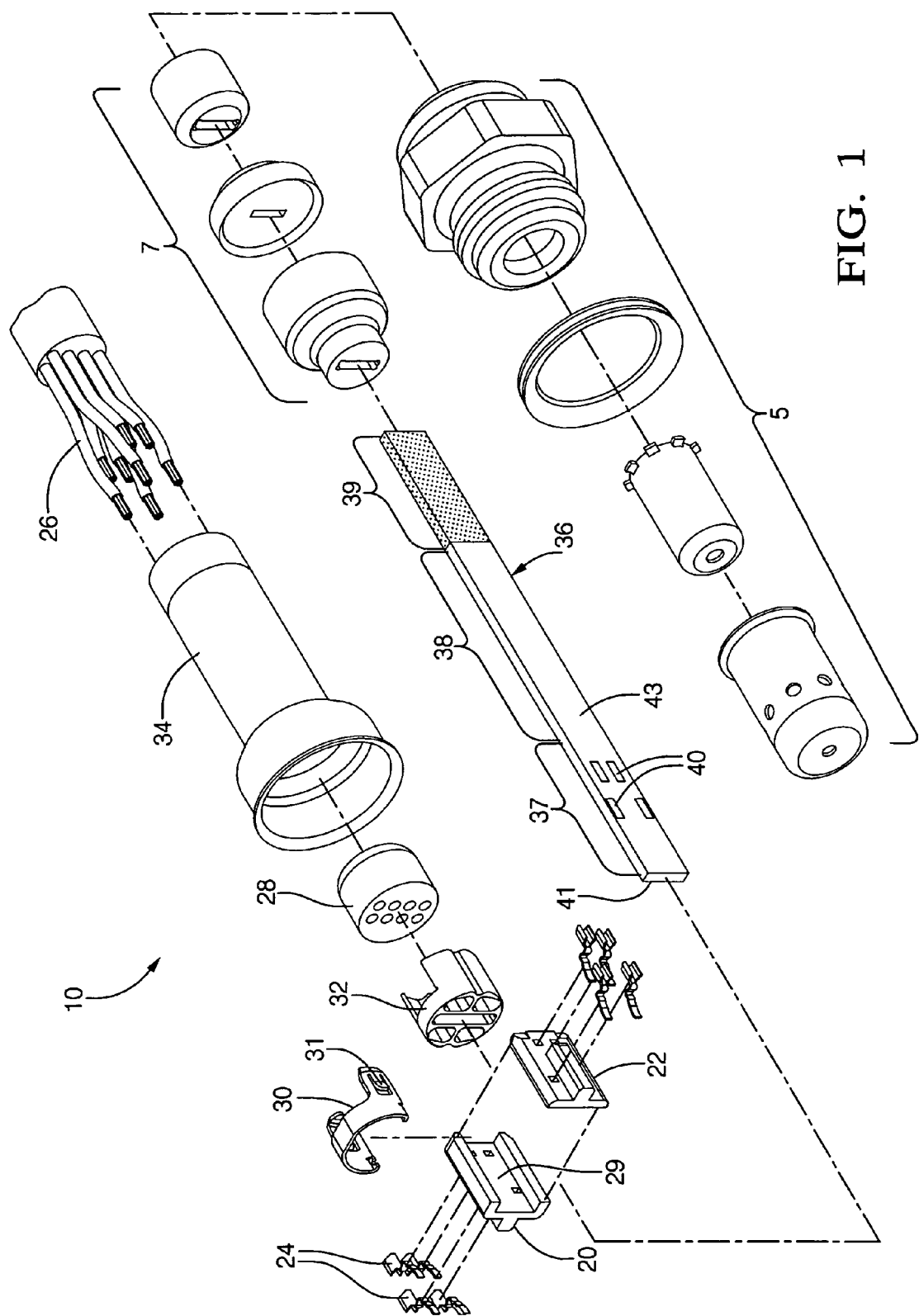
FIG. 1 is a schematic diagram (exploded view) in accordance with the present invention.

Referring now to the drawing, wherein the showings are for the purpose of illustrating the invention only and not for the purpose of limiting the same, FIG. 1 shows an exploded schematic view of an exemplary connector assembly for a planar sensing element 36 of an exhaust gas sensor 10 which has been constructed in accordance with an embodiment of the present invention.

The exemplary exhaust gas sensor 10 includes a shell assembly 5 into which the planar sensing element 36 assembled. The sensing element 36, described in greater detail hereinafter, has a first end 37, a mid-section 38, and a second end 39. The second end 39 comprises the sensing portion, and is preferably located in a manner to be exposed to the exhaust gas feedstream, to monitor the feedstream. The mid-section 38 is inserted within a lower insulator, talc pack and upper insulator 7 which are operable to completely effectively seal the sensing element at its interface with the shell assembly 5 so only the second end is exposed to exhaust gases, and decouple the sensing element thermally and mechanically from the shell assembly 5. Overall, exhaust gas sensor assemblies are known to one skilled in the art.

The planar sensing element 36 of this embodiment comprises an elongated ceramic element, rectangular in shape, and having a square cross-section. The major width is approximately six (6) millimeters at first end 37 with a depth of 1.3 millimeters, and is typically fifty millimeters in length. The sensing element 36 is designed to monitor NOx gases and exhaust gas air/fuel ratio, requiring eight electrical connections. Each of the eight electrical connections comprises a contact pad 40 at a terminal point near the first end 37 of the sensing element 36. In this embodiment, there are four contact pads 40 arranged on a nominal top, or first half 41 of the sensing element 36 and four contact pads 40 similarly arranged on a nominal bottom or second half 43 of the sensing element 36. The contact pads 40 on the top 41 and bottom 43 are each preferably arranged in two rows, with two pads per row. Planar sensing elements having contact pads on both sides of the element body are known to one skilled in the art.

The exemplary connector assembly comprises a pair of ceramic clamshells 20, 22, a plurality of terminals 24, a plurality of electrical lead wires 26, a spacer 32, a seal 28, and a retaining clip 30, with an upper shield 34 of the sensor.

The connector assembly for the exemplary exhaust gas sensor 10 includes the eight lead wires 26 from a wiring harness (not shown), which electrically connect to an engine controller (not shown). The lead wires 26 are used to provide electrical energy from the controller to a heater element assembled into the sensing element 36, to provide a biasing current for signal generation through the sensing element 36, to monitor outputs of the sensing element, and to provide isolated signal grounding.

The ceramic clamshells 20, 22, preferably comprise an opposed pair of ceramic clamshells, and each clamshell is designed to mechanically retain and electrically isolate a plurality of terminals 24. In this embodiment there are four terminals 24 retained by each clamshell 20, 22. Each of the clamshells includes four pass-through openings 29 that pass from an inside portion of the clamshell to the outside portion, are preferably rectangularly shaped, and designed to accommodate insertion of one terminal 24. Each of the openings 29 is placed in each clamshell 20, 22 so one of the terminals 24 aligns with one of the contact pads 40 upon assembly of the planar sensing element 36 with the connector assembly. Alignment of the terminals 24 ensures that each terminal is able to electrically conductively mate to the corresponding contact pad 40 of the planar sensing element 36.

Figure 3:
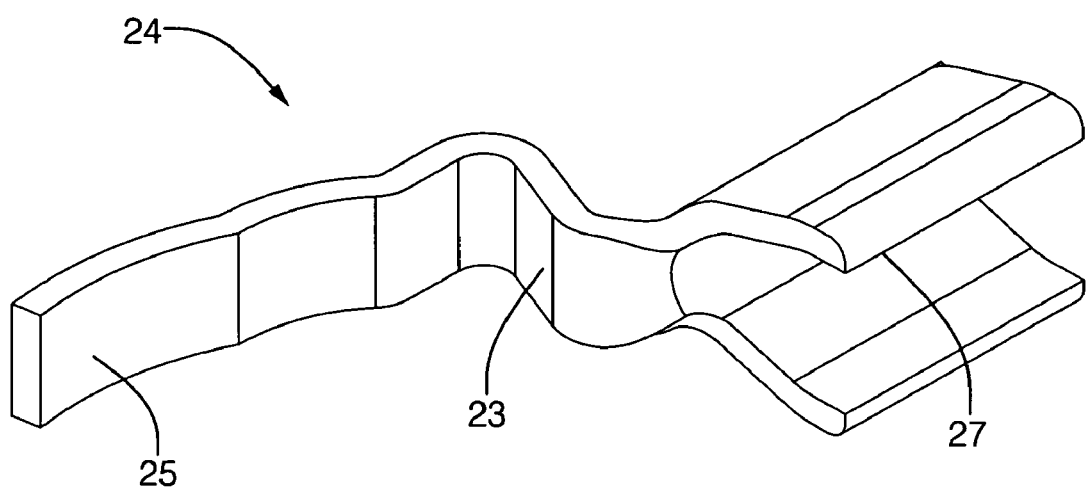
FIG. 3 is a schematic diagram, in accordance with the present invention.

Referring now to FIG. 3 in conjunction with FIG. 1, the terminal 24, in accordance with the invention, is shown. Each terminal 24 used in the connector assembly is preferably a common mechanical design, allowing the use of a common part number to reduce manufacturing costs and errors. Each terminal is preferably manufactured from 300-series stainless steel material, with gold plating on the contact area to improve conductivity of the terminal over its life. Overall shape of the terminal 24 is described as "z"-shaped, wherein a blade portion 25 is inserted into the opening 29 of the clamshell of the connector assembly, and a connector portion 27 remains on the outside of the clamshell for connection to one of the electrically conductive lead wires 26. The terminal includes a step portion 23 which corresponds to the shape of opening 29 of the clamshell, permitting transition of the terminal 24 through the clamshell 20, 22 and effectively locking the terminal into the clamshell when tension is applied using the lead wire 26 in combination with the spacer 32 and upper seal 34, as described hereinafter. Each lead wire 26 is preferably connected to each terminal 24 by crimping the connector portion 27 of the terminal onto the lead wire 26, as is common and known to one skilled in the art. The blade portion 25 of the preferred terminal design may include a compound bend wherein the terminal 24 continues past the bend back towards the clamshell 20, 22. Continuing the curve back towards the clamshell 20, 22 prevents snagging of terminal ends prior to and during assembly, and increases bend strength of the terminal. The compound bend provides pressurized mechanical contact with the corresponding contact pad 40 over the life of the sensor 10. This is part of design robustness of the connector assembly intended to accommodate and tolerate variations in the manufacturing process that could otherwise reduce durability and performance of the sensor 10.

Each of the plurality of electrical lead wires 26 is preferably made of wire intended for high temperature, high vibration applications. In this embodiment, a nickel-plated, multi-stranded copper wire is used with an automotive-grade insulation material such as a fluorinated hydrocarbon, for example, polytetrafluoroethylene (PTFE), which is a polymer with characteristics of high temperature, and low-permeability, and is capable of withstanding temperatures in excess of 260° C. This wire is a readily available automotive-grade wire that may be used with the aforementioned terminals. A common lead wire 26 is used for each of the connections in order to reduce errors in manufacturing and improve robustness of the sensor. Furthermore, each of the lead wires 26 is preferably of a distinct and different color.

The spacer 32 comprises a device that is preferably positioned between the opposed pair of ceramic clamshells 20, 22 and seal 28. Upon assembly of the connector assembly to the sensing element 36, the spacer 32 effects position assurance to seal 28. The spacer necessarily effects position of the seal 28 within the upper shield 34 upon assembly to the shell assembly 5, due to placement and assembly of the shield 34 upon the shell assembly 5, and the placement of the seal 28, the spacer, the opposed clamshells, and the sensor element in the shell assembly 5. The electrically conductive lead wires 26 preferably pass through the spacer 32 to mechanically secure and electrically isolate each electrical connection to each of the terminals 24. The spacer physically secures each of the terminals in the corresponding ceramic clamshell, prior to assembly, by maintaining tension on the wires. Mechanical tension is created through a slip fit when the lead wires 26 are passed through openings in the seal 28. The spacer 32 limits movement of wires and thereby prevents wire fatigue. By attaching lead wires 26 to terminals 24, inserting the terminals 24 into each clamshell 20, 22, passing the lead wires 26 through the spacer 32 and subsequently through openings in the seal 28, and tensioning the lead wires 26 through the interference of the wire leads passing through the seal, the terminals are secured in the clamshell devices prior to sensor assembly. Furthermore, a hinge point is preferably created between the clamshell devices 20, 22 prior to assembly of the connector assembly to the shell 5 with the planar sensing element 36 of the exhaust gas sensor 10. In assembling the connector assembly with the clamshells in the hinged configuration prior to assembly, the sensing element 36 is inserted into the connector assembly, until the clamshells 20, 22 abut the upper insulator 7, without physical contact between the contact pads 40 and the terminals 24. After inserting the sensing element 36 into the connector assembly, the opposed clamshells 20, 22 are physically closed around the sensing element 36, compressive force is applied and the clip 30 is attached around the opposed clamshells to maintain the compressive force. At this point during assembly, the pads 40 and terminals 24 mate in physical contact. This reduces or effectively eliminates wear on the pads 40 and terminals 24 due to assembly, and decreases or eliminates risks of electrical interference or cross-talking due to scraping and transfer of trace materials off of either the contact pad 40 or the terminals. The described assembly process allows use of greater amount of compressive force to close the opposed clamshells, because the amount of compressive force used in this assembly does not have to be tempered or reduced by concerns related to wear on the terminals and pads caused during insertion process found during a typical connection assembly. The spacer is preferably made of materials that are durable over temperatures ranging from −40° C. to over 300° C. without excessive thermal expansion, including ceramic or high-temperature thermoplastics.

The seal 28 is mechanically pressed against the spacer 32, and the upper shield 34 is placed over the seal and assembled connector. The seal 28 comprises an elastomeric device with the plurality of electrically conductive wires passing therethrough. The seal 28 operates to substantially effectively seal the connector assembly within the upper shield 34. It is preferably made of material capable of maintaining a seal under high temperature operation. In this embodiment, the seal is a fluoroelastomer material rated at 230° C. continuous operation, and up to 280° C. for up to approximately fifty hours of operation. Seal design and material selection for this application is known to one skilled in the art.

The retaining clip 30 is preferably a single piece metal ring operable to bind together the opposed pair of ceramic clamshells. After the planar sensing element is inserted therebetween, the opposed pair of ceramic clamshells are closed and placed under compression force, and the retaining clip 30 is attached around them. The retaining clip 30 is designed to include several structural tabs 31 radiating outwardly from the body of the retainer clip 30.

Figure 2:
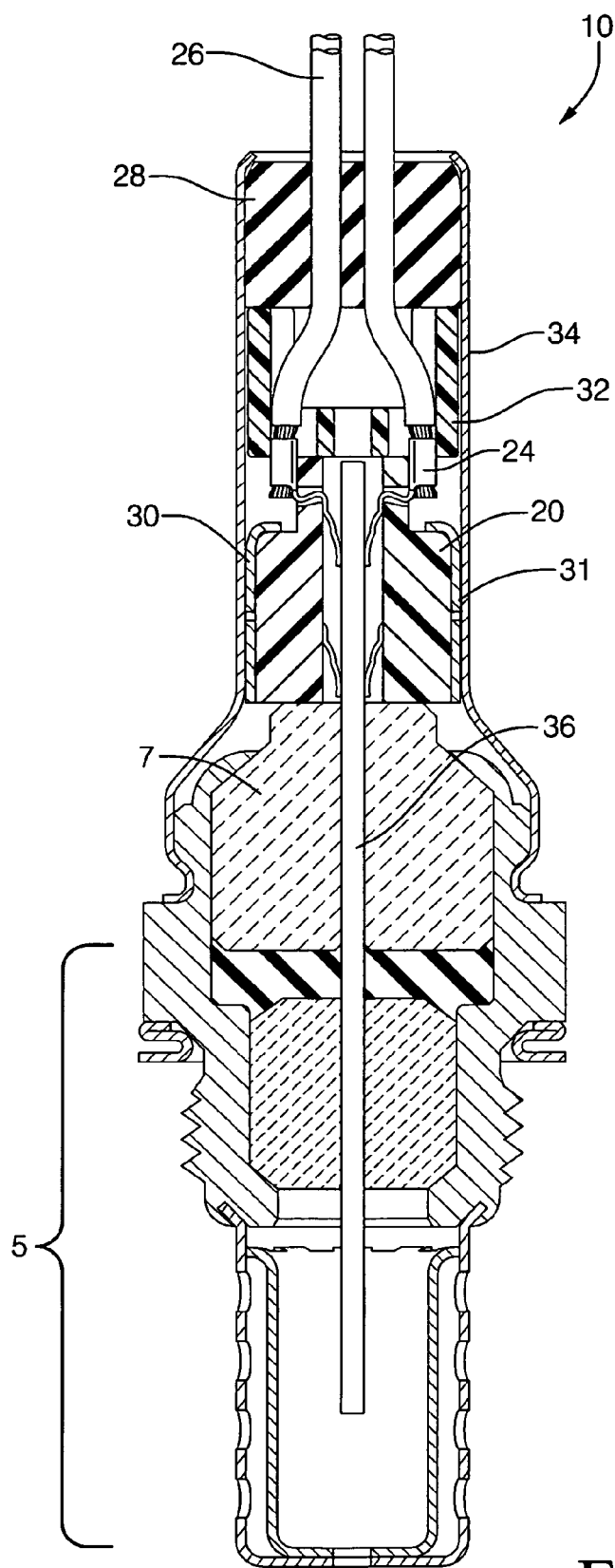
FIG. 2 is a schematic diagram, in accordance with the present invention.

Referring now to FIG. 2, the assembled connector assembly with the retaining clip is designed so an outside diameter of the retaining clip with structural tabs 31 is greater than a corresponding inside diameter of the upper shield, to create an interference fit between the structural tabs 31 and the upper shield 34. Therefore, when the upper shield 34 is assembled onto the assembled connector assembly, the interference between the structural tabs 31 and the upper shield 34 creates additional compressive force which is transferred to the interfaces between the terminals and the connector pads 40 of the sensing element, thus improving connectivity and electrical conductivity therebetween, improving robustness of the sensor electrical connection.

Although this is described as a connector assembly for an exhaust gas sensor, it is understood that alternate embodiments of this invention can include any application wherein there is a need to provide a durable sensor connecting scheme for use with densely packed lead wire connections in a high temperature environment. The invention has been described with specific reference to the preferred embodiments and modifications thereto. Further modifications and alterations may occur to others upon reading and understanding the specification. It is intended to include all such modifications and alterations insofar as they come within the scope of the invention.

Having thus described the invention, it is claimed:

1. A connector assembly for a planar sensing element of an exhaust gas sensor, comprising:
   an opposed pair of ceramic clamshells, each clamshell operable to mechanically retain and electrically isolate a plurality of terminals; at least one of the clamshells including at least one hole extending through the clamshell, said hole defined by a contiguous boundary of the ceramic of said at least one clamshell, with one terminal passing through the hole; each terminal electrically conductively mating to one of a plurality of corresponding contact pads of the planar sensing element; each terminal electrically and mechanically connected to one of a plurality of electrically conductive lead wires;
   a spacer, positioned between the opposed pair of ceramic clamshells and a seal, each of the plurality of electrically conductive lead wires passing through the seal and the spacer; and,
   a retainer clip, operable to bind together the opposed pair of ceramic clamshells;

wherein the opposed pair of ceramic clamshells, the spacer, the seal, and the retainer clip are contained within an upper shield.

2. The connector assembly of claim 1, wherein the spacer is operable to mechanically secure each electrically conductive lead wire and electrically isolate each electrical connection to each of the terminals.

3. The connector assembly of claim 2, wherein the spacer is operable to substantially physically secure each of the terminals in the corresponding ceramic clamshell.

4. The connector assembly of claim 3, wherein the spacer creates a hinge point between the clamshells prior to assembly of the connector assembly to a shell which houses the planar sensing element of the exhaust gas sensor.

5. The connector assembly of claim 4, wherein an upper insulator operably connected to the planar sensing element effects a position assurance of the sensing element and opposed pair of clamshells upon assembly of the connector assembly to the planar sensing element of the exhaust gas sensor.

6. The connector assembly of claim 5, wherein the seal inside a distal end of the upper shield comprises an elastomeric device with the plurality of electrically conductive wires passing therethrough, operable to substantially effectively seal the connector assembly within the upper shield.

7. The connector assembly of claim 1, wherein the retainer clip operable to bind together the opposed pair of ceramic clamshells is operable to maintain the opposed pair of ceramic clamshells under compression force when a first end of the planar sensing element is placed therebetween.

8. The connector assembly of claim 1, wherein the planar sensing element with the plurality of corresponding contact pads comprises a first half of the plurality of corresponding contact pads on a first planar side of the planar sensing element and a second half of the plurality of corresponding contact pads on a second planar side of the planar sensing element.

9. The connector assembly of claim 8, wherein the planar sensing element includes eight contact pads.

10. An exhaust gas sensor, comprising a planar sensing element housed within a shell and a connector assembly; the connector assembly comprising:
an opposed pair of ceramic clamshells, each clamshell operable to mechanically retain and electrically isolate a plurality of terminals; at least one of the clamshells including at least one hole extending through the clamshell, said hole defined by a contiguous boundary of the ceramic of said at least one clamshell, with one terminal passing through the hole; each terminal electrically conductively mated to one of a plurality of corresponding contact pads of the planar sensing element; each terminal electrically and mechanically connected to one of a plurality of electrically conductive lead wires;
a spacer, positioned between the opposed pair of ceramic clamshells and a seal, each of the plurality of electrically conductive lead wires passing through the seal and the spacer; and,
a retainer clip, operable to maintain a compression fit between the opposed pair of ceramic clamshells when a first end of the planar sensing element is placed therebetween;

wherein said opposed pair of ceramic clamshells, spacer, seal, and retainer clip are contained within an upper shield sealably connected to the shell.

11. The exhaust gas sensor of claim 10, wherein the retainer clip includes a plurality of tabs extending radially from the retainer clip, said tabs operable to fit interferingly with the upper shield.

12. A method to assemble a connector assembly to a planar sensing element,
said planar sensing element having a plurality of contact pads near a first end of the planar sensing element, wherein half of the plurality of contact pads are on a first planar side and half of the plurality of contact pads are on a second planar side of the planar sensing element;
said connector assembly comprising an opposed pair of ceramic clamshells, each clamshell having a plurality of holes extending through the clamshell, at least one of said holes defined by a contiguous boundary of the ceramic of said at least one clamshell, and a plurality of terminals, each terminal passing through one of the plurality of holes, each terminal corresponding to one of the plurality of contact pads of the planar sensing element, each terminal electrically and mechanically connected to one of a plurality of electrically conductive lead wires; and, a spacer positioned between the opposed pair of ceramic clamshells and a seal, wherein each of the plurality of electrically conductive lead wires pass through the seal and the spacer; the assembly comprising:
assembling the connector assembly, wherein the spacer substantially secures each of the terminals in the corresponding ceramic clamshell, and, wherein the spacer creates a hinge point between the opposed pair of clamshells;
inserting the first end of the planar sensing element between the opposed pair of clamshells so tat each of the clamshells substantially abuts an upper insulator operably physically connected to the planar sensing element;
closing the opposed pair of clamshells, causing each of the terminals in the corresponding ceramic clamshell to mate with one of the plurality of contact pads of the planar sensing element;
applying a compressive force to the opposed pair of clamshells; and,
securing the compressed opposed pair of clamshells with a retainer clip.

13. The method of claim 12, further comprising:
inserting the connector assembly assembled to the planar sensing element into an upper shield; and,
attaching sealably the upper shield to a shell housing the connector assembly assembled to the planar sensing element.

14. The method of claim 12, further comprising:
securing the compressed opposed pair of clamshells with the retainer clip, said retainer clip having a plurality of radially extending tabs;
inserting the connector assembly assembled to the planar sensing element into an upper shield; and,
creating a compressive force upon the connector assembly assembled to the planar sensing element, said compressive force effected by an interference fit with the radially extending tabs of the retainer clip and the upper shield.

* * * * *